United States Patent [19]

Hudimac, Jr.

[11] Patent Number: 4,860,765
[45] Date of Patent: Aug. 29, 1989

[54] AIR FLOW SENSOR

[75] Inventor: George S. Hudimac, Jr., Allentown, Pa.

[73] Assignee: Mechanical Service Co. Inc., Allentown, Pa.

[21] Appl. No.: 103,359

[22] Filed: Oct. 1, 1987

Related U.S. Application Data

[63] Continuation of Ser. No. 862,291, May 12, 1986, abandoned.

[51] Int. Cl.$^4$ ............................................. A61B 5/08
[52] U.S. Cl. ............................ 128/725; 128/204.23; 137/516.17; 73/861.55
[58] Field of Search ...... 128/716, 725, 204.23–204.24, 128/206.15, 121.28, 207.12; 73/861.47, 861.55–861.57; 137/554, 512.3, 516.15, 516.17, 516.19, 516.21, 516.23

[56] References Cited

U.S. PATENT DOCUMENTS

| | | | |
|---|---|---|---|
| 2,311,375 | 2/1943 | Farwick | 73/861.57 |
| 2,439,614 | 4/1948 | Schramm | 73/861.57 |
| 2,475,630 | 7/1949 | Melas et al. | 73/861.57 |
| 2,779,194 | 1/1957 | Slettenmark | 73/861.57 |
| 3,232,288 | 2/1966 | Krobath | 128/725 |
| 3,383,484 | 5/1968 | Arp et al. | 128/204.23 |
| 3,504,542 | 4/1970 | Blevins | 128/725 |
| 4,283,798 | 8/1981 | Kuehn | 33/333 X |
| 4,509,551 | 4/1985 | Luper | 128/204.23 X |
| 4,546,793 | 10/1985 | Stupecky | 128/725 |

Primary Examiner—Kyle L. Howell
Assistant Examiner—Angela D. Sykes
Attorney, Agent, or Firm—Frederick J. Olsson

[57] ABSTRACT

The invention contemplates an improved air flow sensor including a proximity switch which has a metal disk mounted with respect to the sensing face to be movable by air flow in the action zone of the magnetic field as between a position adjacent the sensing face to a position away from the face or visa versa whereby the switch oscillator is off and on respectively at the two extremes to provide an indication of the condition. The air flow sensor is shown herein in apparatus to calculate breathing rate, in object detection apparatus, and in vacuum lift apparatus.

11 Claims, 4 Drawing Sheets

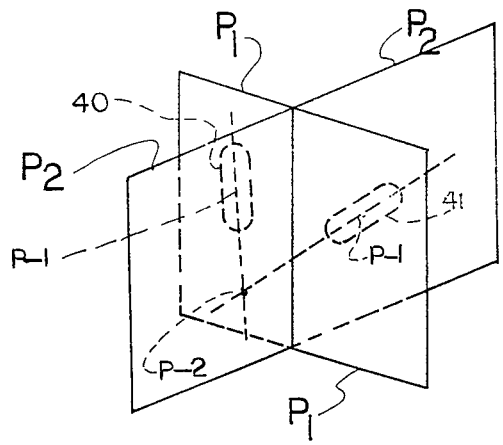
FIG. 4A
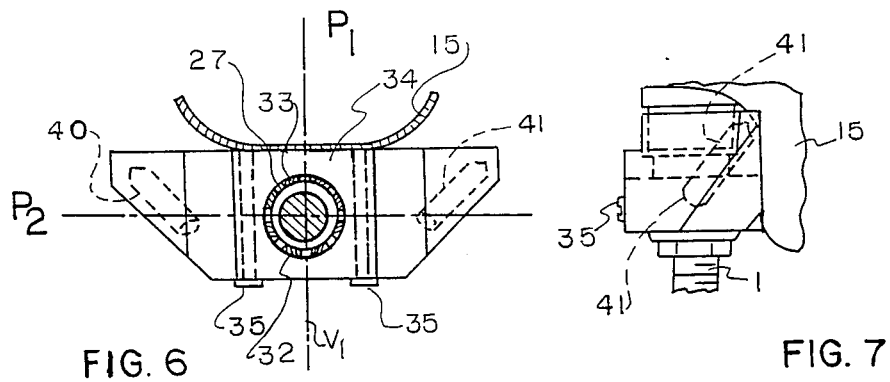
FIG. 6
FIG. 7
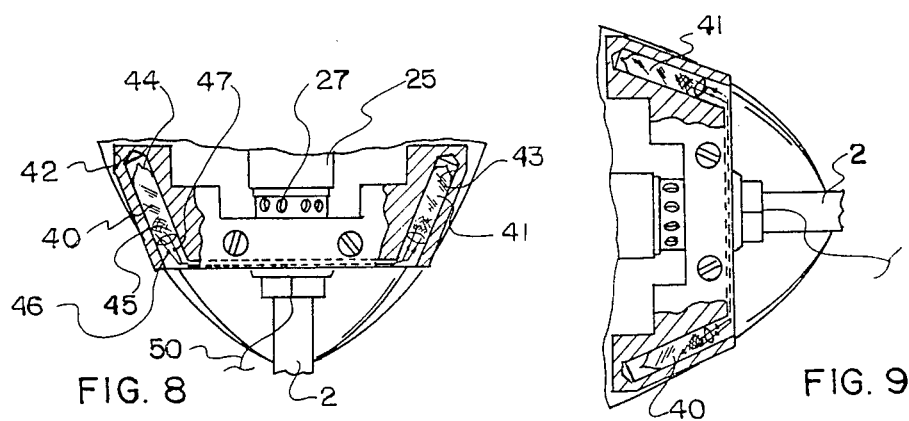
FIG. 8
FIG. 9

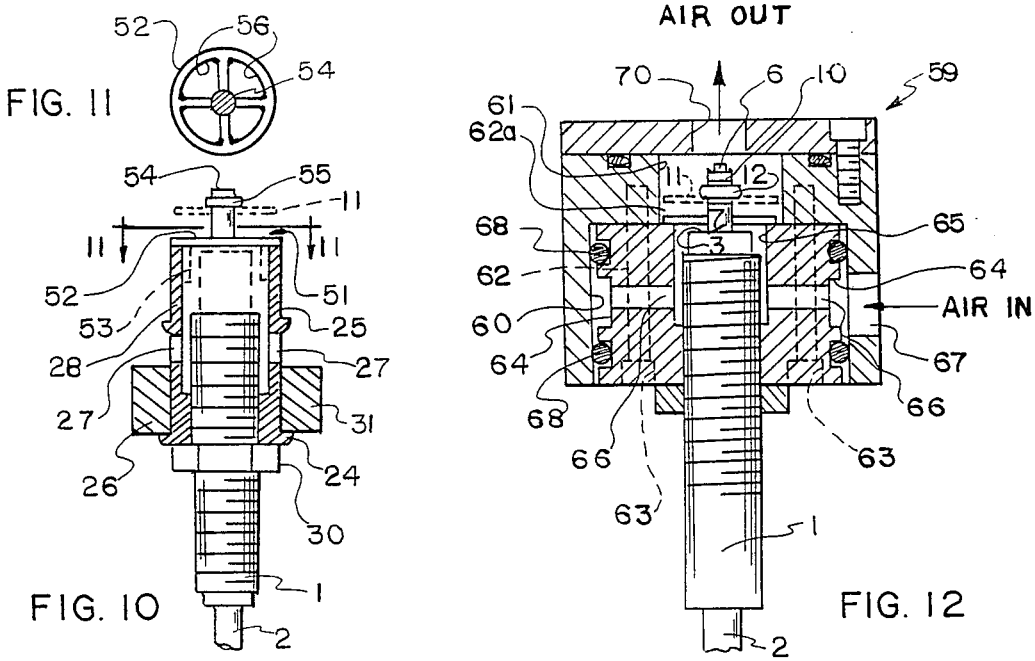
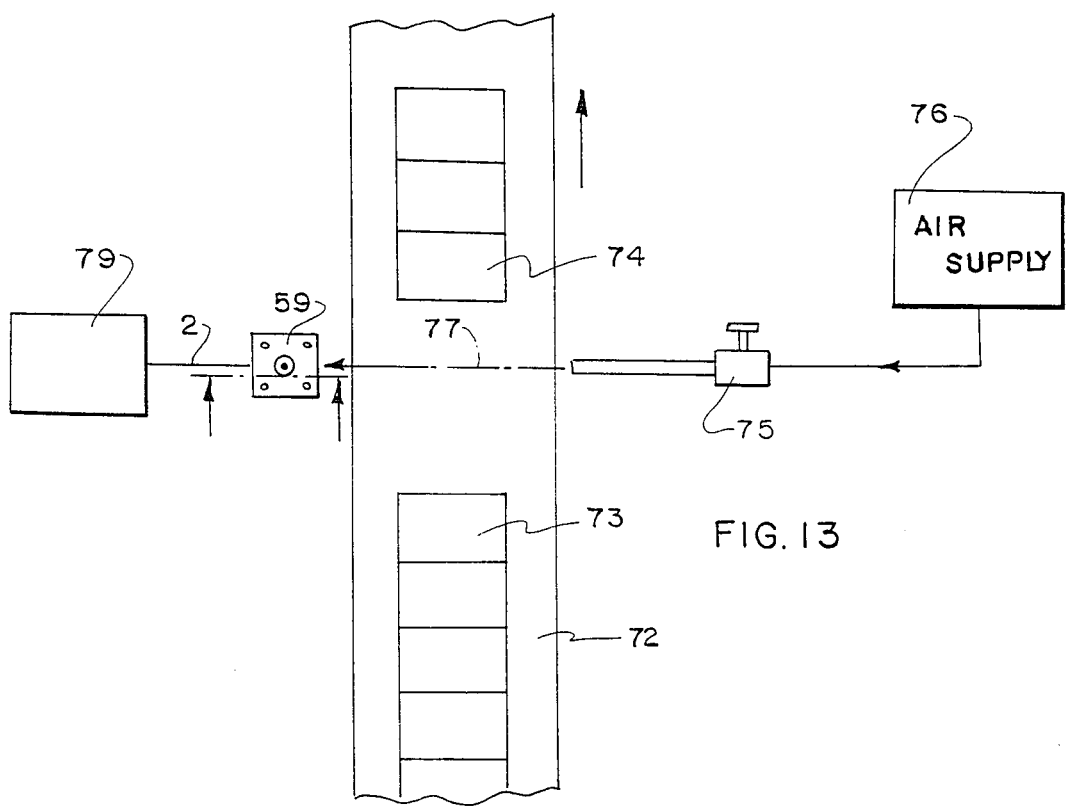

4,860,765

AIR FLOW SENSOR

This application is a continuation of my copending application Ser. No. 862,291 filed May 12, 1986, now abandoned.

SUMMARY OF THE INVENTION

The invention relates in general to control devices and in particular relates to an improved air flow sensor to be mounted in the path of an air stream.

One of the principal objectives of the invention is to promote the useful art of air flow sensors by providing an improved sensor to be mounted in the path of an air stream and operate when the air is flowing or not flowing to detect the flow or non-flow and to detect the direction of flow and accordingly generate a signal which signifies the particular condition.

More specifically, the invention contemplates an improved air flow sensor including a proximity switch which has a metal disk mounted with respect to the sensing face to be movable by air flow in the action zone of the magnetic field as between a position adjacent the sensing face to a position away from the face or visa versa whereby the switch oscillator is off and on respectively at the two extremes to provide an indication of the condition.

The invention has special utility in connection with breath detection equipment to detect each time a patient inhales or exhales and to provide a signal which can be fed to means for calculating the inhalation or exhalation rates and in connection with industrial applications such as object detection equipment and vacuum lift equipment.

BRIEF DESCRIPTION OF THE DRAWINGS

The air flow sensor and the breath detection means, the object detection equipment and the vacuum lift equipment employing the sensor will be described below in connection with the following drawings wherein:

FIG. 4A is a diagramatic view illustrating the orientation of mercury switches used in the equipment of FIGS. 4–9;

FIG. 6 is a view taken along the lines 6—6 of FIG. 4;

FIG. 7 is a view taken along the lines 7—7 of FIG. 4;

FIG. 8 is a fragmentary view partially in section illustrating the operation of the mercury switches employed in the equipment of FIG. 3;

FIG. 9 is a fragmentary view partially in section further illustrating the operation of the mercury switches employed in the equipment of FIG. 3;

FIG. 10 is an elevational view partially in section illustrating a modification of the air flow sensor;

FIG. 11 is a view taken along the lines 11—11 of FIG. 10;

FIG. 12 is an elevational view partially in section illustrating a modified air flow sensor;

FIG. 13 is a view illustrating an object detection system;

DESCRIPTION OF THE PREFERRED EMBODIMENTS

Figure 1:
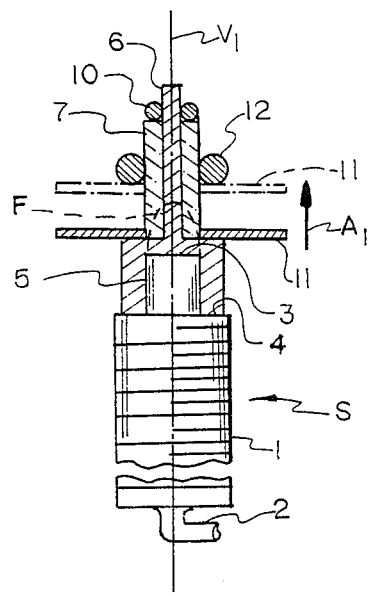
FIG. 1 is a view partially in section illustrating the air flow sensor arranged in vertical orientation.
Figure 2:
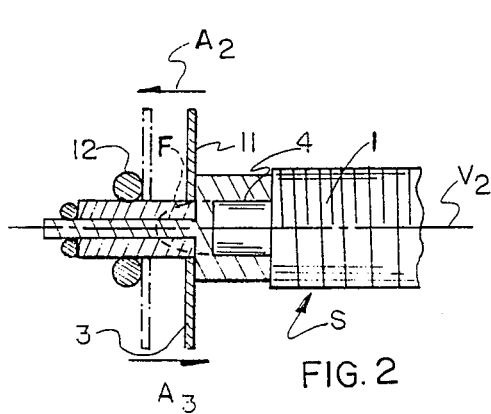
FIG. 2 is a view partially in section illustrating the air flow sensor arranged in a horizontal orientation.

Referring to FIGS. 1 and 2, I have shown a form of the air sensor to detect the flow or non-flow and to detect the direction of air flow. The sensor employs a proximity switch S.

A proximity switch per se is a well-known conventional device of the inductive or capacitive type providing contactless sensing and contactless switching output. The inductive type detects the presence or non-presence of metal objects while the capacitance type detects the presence or non-presence of non-metal solids and liquids.

The proximity switches as applied herein are of the inductive type. These switches have a housing which is typically made of plastic selected as a function of the environment where the switch will be used. The housing carries coil and core means arranged so that upon energizing of the coil means, a magnetic field usually in the form of a parabolic cone appears adjacent the exterior of the sensing face. The coil is part of the RF oscillator. When a metal object is outside of the field, the oscillator will run in its normal fashion. When a metal object enters the field, the object will absorb energy and when enough energy is absorbed so that the field is weak enough, the oscillator will stop. The difference between the oscillating and non-oscillating condition represents the presence or non-presence of a metal object.

The sensor of the present invention is based on the idea of supporting a piece of metal for constrained movement into and out of the magnetic field as a function of air flow. Normally, the metal piece preferably is a thin steel disk. The disk is arranged so that it can be moved by air flow as between a position in the field so that the oscillator is in off condition and a position in or out of the field where the oscillator runs normally.

Normally, the above positions will be a position closely adjacent to or engaging the sensing face and a position out of the field or in the field to a degree that it does not absorb sufficient energy to stop the oscillator.

The invention contemplates that the weight and cross-sectional area of the disk provide that when the disk is arranged to move along a vertical axis vertical air flow will move the disk upwardly and, in the absence of air flow, gravity will move the disk downwardly. The invention contemplates that the disk be arranged to move along a horizontal axis where air flow in one direction will move the disk in that direction. In connection with horizontal orientation, when air is unidirectional spring means may be employed which will allow the disk to be moved by air flow in one direction and upon the absence of air flow will move the disk to its original position.

With the above in mind, I now turn to the detailed description.

In FIG. 1, a proximity switch S has a cylindrically, shaped housing 1. The housing contains coil and core elements (not shown), the conductors for which are in cable 2, and the surface on one end of the housing is the sensing surface 3. The housing is formed with a shoulder 4. As noted the sensor is oriented so that its axis $V_1$ extends vertically.

On the shoulder 4 is an end piece comprising a cap portion 5 and a post portion 6. As will be observed, the post portion is adjacent to and extends vertically away from the sensing surface 3. The end piece is made of non-magnetic material such as Plexiglass plastic and is press-fitted on the shoulder 4. The post portion 6 carries a glass tube 7 which is press-fitted on the post portion as shown or is slip-fitted and held in position by rubber O-ring 10. The glass tube 7 carries a metal thin disk 11 and a rubber O-ring 12. The disk 11 can reciprocate back and forth as between the sensing face 3 and the O-ring 12.

The O-ring 12 is positioned in the glass tube 7 so that when the disk 11 engages the same, the disk 11 is positioned out of the magnetic field F at the sensing face. In this position, the switch oscillator will run. When the disk 11 is engaged with sensing face 3, the switch oscillator has ceased or will cease operation.

The weight of the disk 11 and its cross-sectional area are chosen so that air flow as indicated by arrow $A_1$ in a vertical direction, will lift the disk up against the abutment or O-ring 12. When air flow ceases, the weight of the disc will cause the same to move down the tube 7 and engage the sensing face 3. The aperture in the disk has sufficient clearance with the tube 7 so that no constraints as to the above movement are developed. In connection with movement of the disk 11, the purpose of the glass is to provide a smooth non-cuttable surface.

It will be readily apparent that the non-oscillating condition of the switch oscillator can be used as an indicator that air flow has stopped and that the oscillating condition can be used as an indication that air is flowing.

In FIG. 2 I have shown the sensor of FIG. 1 oriented so that its axis $V_2$ extends horizontally. In FIG. 2 parts which correspond to those shown in FIG. 1 are designated by the same numbers.

The arrangement of FIG. 2 can be employed to detect the direction of air flow. For example, if air is moving in the direction indicated by the arrow $A_2$, the disk 11 will be moved from the position shown by full lines to the position shown by the dotted lines. The operating condition of the oscillator can be employed to indicate such flow direction. If the air flow is reversed in the direction of the arrow $A_3$, the disk 11 will be moved to the position shown by the full lines and the non-operation condition of the oscillator used to indicate the condition.

The single direction air flow, the sensor of FIG. 2 is modified as by compression spring (not shown) over the glass tube 7 and extending between the abutment 12 and the disk 11. The function of the spring to hold the disk 11 against the sensing face 3 but to yield upon the flow of air in the direction of the arrow $A_2$ to permit the disk to be moved back adjacent the abutment 12 where it will be located with respect to the field F such that the oscillator operates. Naturally, the position of the abutment 12 is chosen to achieve the foregoing condition. The spring can be made of metal since it is out of the field F. Also the spring has a low spring constant; i.e. very little force to make it compress a large distance.

With the above in mind, I will now describe the use of the sensor in patient breathing detection.

Figure 3:
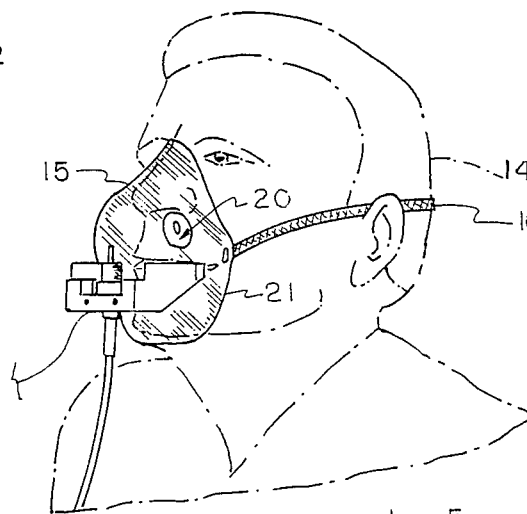
FIG. 3 is a perspective view illustrating the air flow sensor incorporated in breath detection equipment.
Figures 4, 5:
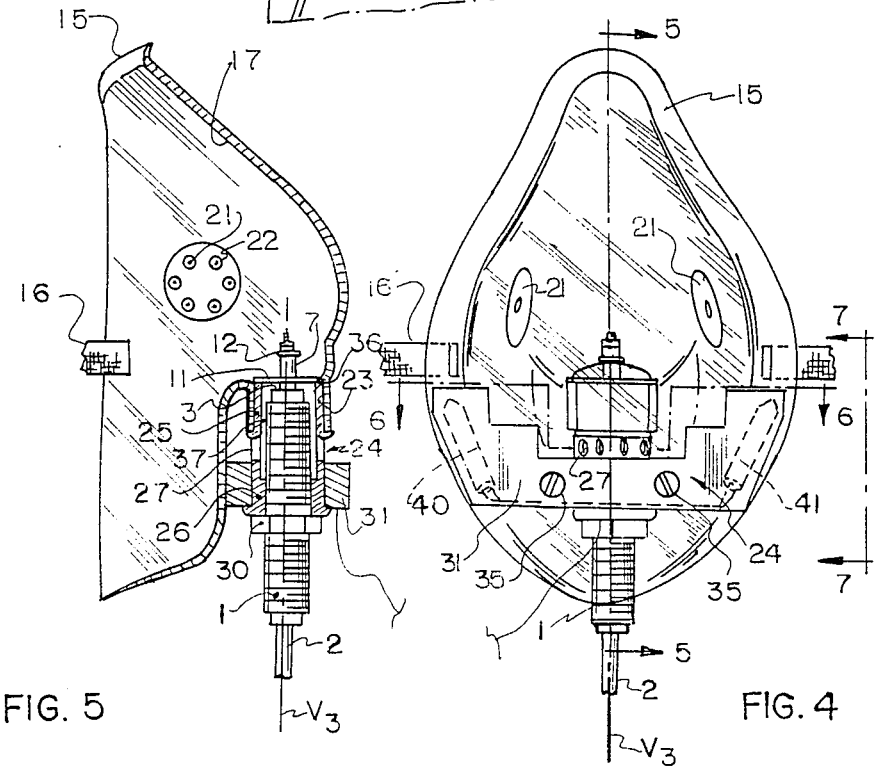
FIG. 4 is a front elevational view of the equipment of FIG. 3.
FIG. 5 is a view taken along the lines 5—5 of FIG. 4.

In FIG. 3 the head and shoulders of a person are represented by the dotted lines 14. On the face of the patient is a mask 15 held in place by the strap 16. The mask per se is made of transparent flexible plastic and covers the nose and mouth of the person and makes relatively close contact with the face to form a hollow inside chamber 17. The mask has check valves 20 each comprising an outside flapper 21 covering holes 22 by which air can exit from the chamber but not enter. On the bottom of the mask is an air intake tube 23 forming a mask air inlet through which air, when the patient breathes, flows into the chamber (FIG. 5). The foregoing parts of the mask 15 are conventional.

The invention contemplates that the air flow sensor be mounted on the air intake tube 23 to detect the flow of air through the tube when the patient breathes and to essentially cut off the exit of air through the tube 23 when the patient exhales (and in doing so the air exits through the check valves 20). The manner in which this is done will now be described in connection with FIGS. 3 through 9.

The arrangement of FIGS. 3 through 9 employs the type of sensor shown in FIG. 1 and the same numbers as used in FIG. 1 to identify parts are used in FIGS. 3 through 9.

An elongated tubular member 24 has a top section 25 and a bottom section 26. The top section 25 is tightly press-fitted into the air intake tube 23. Between the top section 25 and the bottom 26 are formed a plurality of air inlets 27. The bottom section 26 is internally threaded and carries the housing 1 which, of course, is externally threaded. A nut 30 holds the housing 1 in the desired position. The bottom section 26 also carries a support member 31.

The manner in which the support is secured to the bottom section is best shown in FIG. 6. The support member 31 has a semi-circular cavity 32 which surrounds one-half of the bottom section 26. The other half of the bottom section is secured in a semi-circular cavity 33 of a clamp piece 34. The clamp piece is pulled tight against the bottom section 26 by the screws 35.

As will be seen in FIG. 5, the upper edge of the tubular member forms a seat 36 upon which rests the metal disk 11. As shown, the disk 11 spans the top of the air intake tube 23 and thus covers the mask air inlet. The housing 1 is positioned in the top section 25 so that the sensing face 3 is slightly below the seat 36 and the glass tube 7 and abutment 12 are within the hollow chamber 17 of the mask. The inside diameter of the tubular member 25 is larger than the outside chamber of the housing 1 so as to create a cylindrically-shaped air space 37 between the air inlets 27 and the mask inlet.

The manner in which the mask and sensor function during the time when the patient breathes will next be described.

When the person inhales, the check valves 20 close and air is drawn through the air inlets 27 up through the air space 37 and the metal disk 11 is lifted off of the seat 36 and carried up against the O-ring abutment 12. When the patient stops inhaling, the air flow into the mask stops and the weight of the disc causes the same to move down on the seat 36. With the exhaling, the air pressure in the chamber increases and the check valve 20 opens to exhaust air from the chamber. The metal disk 11 on the seat 36 substantially seals off the air space 37 so that the exhaled air goes out through the check valves 20.

When the metal disk 11 is on the seat 36, the sensor oscillator stops and when the metal disk is up against the O-ring abutment 12, the oscillator runs. It will be readily apparent that the run or no-run condition of the oscillator can be employed to generate a signal which will signify each time a person inhales or alternatively, each time a person exhales.

It is the normal case that when a person's head is upright such as shown in FIG. 3 and the person is sitting, walking, or jogging, the human heart beat rate is greater than when the person is lying prone on the back or the side. The invention provides a means to detect the prone position and consequently develop a corresponding signal which can be used to trigger mechanism to change the beat rate of a mechanical heart to simulate the automatic change which would take place in the human heart as between the upright and prone positions.

The mechanism for detecting the upright and the prone positions will next be described.

The mechanism takes the form of a pair of mercury switches 40 and 41 which are secured in cavities 42 and 43 (FIG. 8) in the support member 31. These switches are of the conventional type and each has a hollow glass bulb within which are a pair of contacts and a small quantity of liquid mercury. For example, the switch 40 has glass bulb 44, the glob of mercury 45, and contacts 46 and 47. The switch 41 has an identical structure. The contacts of the switches are connected in series and the contacts are led out to the common cable 50.

The two mercury switches are oriented in the support 31 in a special way as explained in connection with FIG. 4-A. Assume that planes $P_1$ and $P_2$ intersect along the vertical axis $V_3$. It will be seen, therefore, that the projections of the axis of the switches 40 and 41 intersect the plane $P_1$ at p-1 and intersect the plane $P_2$ at p-2.

With such orientation of the switches 40 and 41, the upright position of a patient's head (FIG. 8) will cause the mercury in each glass bulb to make an electrical connection between contacts. When the person is prone and lying on a side, the mercury in the lowermost switch, say the switch 40 (FIG. 9), will move down the bulb and interrupt the electrical connection between the contact. The mercury in the switch 40 will continue the electrical connection between contacts. If the patient turns on the opposite side, the reverse situation takes place, that is to say, the mercury in the switch 40 interrupts the connection between contacts. While the mercury in the switch 41 continues the electrical connection, the circuit is opened since the contacts are in series.

While I have not shown the switch condition when the patient is prone on the back, it is evident that the mercury in both switches will interrupt the electrical connection between contacts in that position of the patient.

In FIGS. 10 and 11 I have illustrated another way of mounting the metal disk for motion toward and away from the sensing face of the proximity switch. In FIGS. 10 and 11 the parts which are the same as in FIGS. 1-9 are identified by the same numbers.

The top section 25 carries a molded end piece 51 which has top 52 abutting the outer edge of the top section 25 and a skirt 53 which extends down into the top section and makes a tight fit therewith. The top of the housing 1 is cut back and the skirt dimensioned so there is a space 28 between the same to permit upward passage of air from the inlets 27. The end piece 51 also has a post 54 with O-ring abutment 55. The metal disk 11 is slidably mounted on the post.

The top 52 is structured as shown in FIG. 11, that is to say having openings 56 which permit the passage of air from the space 28.

Preferably the end piece is molded from Delrin plastic which provides a hard surface for the disc to slide on or the post structure can include a glass cylinder as previously described.

I will now describe the use of the sensor in object detection apparatus. This will be done in connection with FIGS. 12 and 13.

The sensor includes main housing 59 which has a first cavity 60 and a second cavity 61. A spool 62 is mounted in the first cavity 60 and held in position by screws 63. The spool has a peripheral channel 64 and an inner bore 65 in communication with second cavity 61. The channel 64 and the inner bore 65 are connected by radial air passageways 66. The peripheral channel 64 and the wall of the first cavity 61 form an air chamber which is fed by first air transfer port 67. The O-rings 68 maintain the chamber air tight. Note that the second cavity 61 is in communication with the second air transfer port 70.

As will be observed, the housing 1 of the proximity switch extends into the inner bore 65 to the extent that the sensing face 3 is slightly below top surface 62a of the spool 62 and the post 6 extends into second cavity 61. The area of the top surface 62a around the cavity 65 forms a seat for the disk 11.

In FIG. 13 a conveyor 72 carries groups of objects such as shipping cartons 73 and 74. On one side of the conveyor is located the jet means 75 connected to air supply 76. The jet means 75 forms an air stream indicated by the dotted lines 77. The air sensor of FIG. 12 is set up so that the port 67 is in the path of the air stream 77. The proximity switch cable 2 is connected to a control device 79.

In the condition shown in FIG. 13, the air from the stream 77 enters the port 67 and passes up through the inner cavity 65 and lifting the metal disk 11 up against the abutment 12 and passing through chamber 61 and out the port 70. The foregoing condition signifies, of course, that no objects are passing through the air stream. When an object enters the air stream, the same is interrupted and the metal disk falls down to the position shown by the full lines. This condition indicates that an object is in or passing through the air stream.

In either condition, the go and no-go operation of the oscillator of the proximity switch can be used for control, counting, or other purposes.

Figure 14:
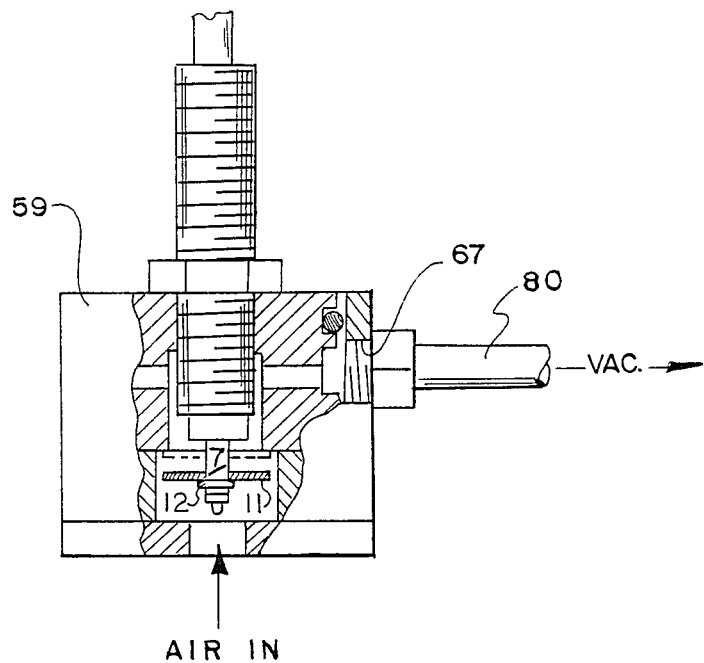
FIG. 14 is a view illustrating the sensor of FIG. 12 in a vacuum lift system.
Figure 15:
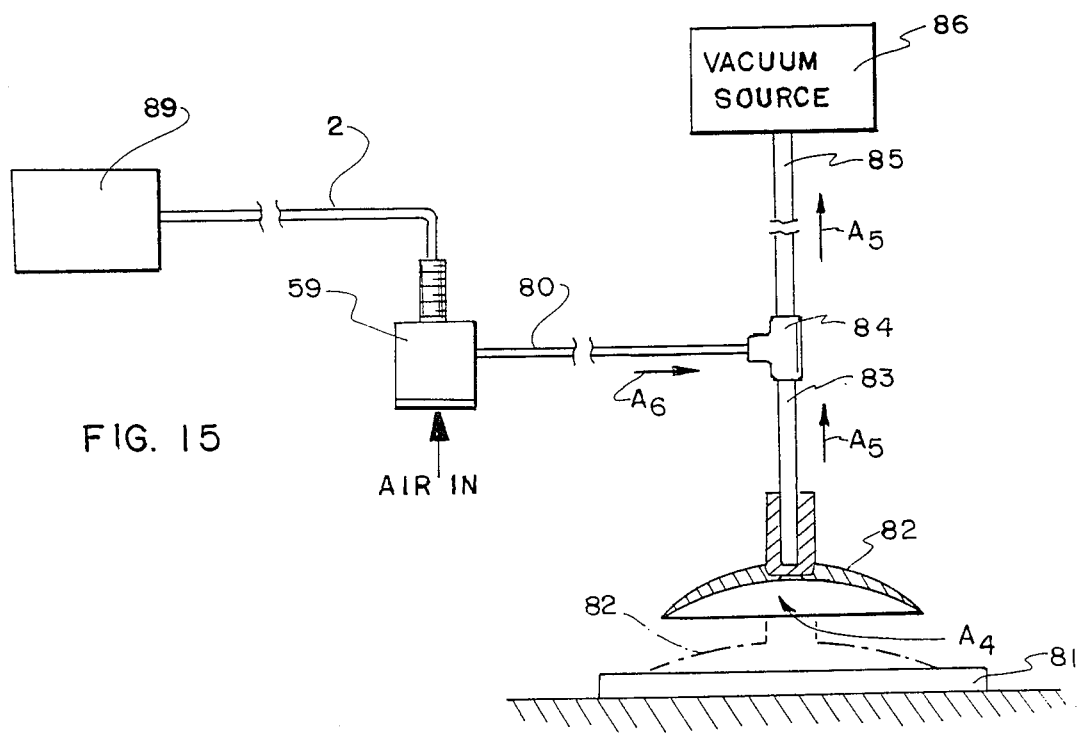
FIG. 15 is a view illustrating a vacuum lift system.

In FIGS. 14 and 15 I have shown how the air flow sensor of FIG. 14 can be employed as a safety signal generator in a vacuum lift system.

In the system of FIGS. 14 and 15 the sensor of FIG. 14 is turned upside down. In the upside down position the port 67 has a fitting and tube 80 connected to first air intake port 67.

In FIG. 15 a load 81 is to be lifted by the vacuum gripper 82, which, through tube 83, fitting 84, and tube 85 is connected to a vacuum source or pump 86 which can draw air as noted by the arrows $A_4$ and $A_5$. The fitting/tube 80 on the sensor is also connected to the fitting 84 so that air is sucked through the tube 80 in the direction of the arrow $A_6$. The proximity switch cable 2 is connected to a control device 89.

In the condition of FIG. 15 air flow through the gripper 82 and back to the vacuum source 86 as indicated by the arrows $A_4$ and $A_5$. Since the air will take the path of least resistance, the vacuum source does not pull air through the sensor and line 80. Thus, the metal disk 11 remains down (due to its weight) on the abutment 12. However, when gripper grips the load 81 as indicated by the dotted lines 82, air flow through the gripper stops and the vacuum pulls air through the sensor and out port 67 via line 80. The air entering the port 70 moves the metal disk up to the position shown by the dotted lines. Since there is some air leakage between the disk and the post 7, the disk is held in position so long as the gripping operation in the load continues. When the lifting operation is completed, the vacuum source 86 is momentarily turned off which allows the gripper to disengage from the load and at that point, the source is turned on and air is sucked through the gripper as indicated by arrow $A_4$. The pressure differential on the disk 12 is reversed and the same falls down to the full line position.

It will be evident that the full-line position of the disk and the dotted line position can be employed to generate corresponding signals to signify that the gripper 82 is functioning to lift the load or not functioning to lift the load.

The mechanical heart control mechanism mentioned heretofore is disclosed in my application entitled MECHANICAL HEART IMPROVEMENTS filed concurrently herewith and having Ser. No. 862,273, pending.

I claim:

1. Air flow sensor means comprising:
   a proximity switch having a housing, one end of which is a sensing face and having means to develop a magnetic field in a zone adjacent the sensing face;
   a shoulder formed on said one end of the housing;
   an end piece comprising a cap portion and a post portion, the cap portion being mounted on said shoulder with the post portion extending away from said sensing face outwardly through said field when the same is present, the end piece being made of non-magnetic material;
   a glass cylinder disposed on said post portion;
   a first rubber O-ring mounted on said glass cylinder;
   a metal disk mounted on said glass cylinder for reciprocating motion toward and away from said sensing face, through said field when the same is present, the metal disk being disposed between said first O-ring and said face and the O-ring functioning as abutment means to prevent the metal disk from sliding off of the glass cylinder, the weight and cross-sectional area of the metal disk permitting the same to be moved on the glass cylinder by the flow of air; and
   a second rubber O-ring mounted on said post portion, the second O-ring functioning to maintain said glass cylinder on the post portion.

2. Air flow sensor means comprising:
   a proximity switch having a housing, one end of which is a sensing face and having means to develop a magnetic field in a zone adjacent the sensing face;
   an end piece including a post portion, the end piece being mounted on said one end of the housing and extending away from said sensing face outwardly through said field when the same is present, the end piece being made of non-magnetic material;
   a glass cylinder disposed on said post portion;
   a rubber O-ring mounted on said glass cylinder; and
   a metal disk mounted on said glass cylinder for reciprocating motion toward and away from said sensing face through said field when the same is present, the metal disk being disposed between said O-ring and said sensing face and the O-ring functioning as abutment means to prevent the metal disk from sliding off of the glass cylinder, the weight and cross-sectional area of said metal disk permitting the same to be moved on the glass cylinder by the flow of air.

3. Air flow sensor means comprising:
   a proximity switch having a housing, one end of which is a sensing face and having means to develop a magnetic field in a zone adjacent the sensing face;
   a metal disk; and
   means mounting said metal disk adjacent said one end for reciprocating motion toward and away from said sensing face through said field when the same is present and including abutment means to limit the movement of the metal disk in a direction away from said face, the weight and cross-sectional area of said metal disk permitting the same to be moved by the flow of air.

4. Air flow sensor means comprising:
   support means;
   a proximity switch mounted on the support means and having a housing, one end of which is a sensing face and having means to develop a magnetic field in a zone adjacent the sensing face;
   an end piece including a post portion, the end piece being mounted on said support means and extending away from said sensing face outwardly through said field when the same is present, the end piece being made of non-magnetic material;
   abutment means on said post portion, the abutment means being made of non-magnetic material; and
   a metal disk mounted on said post portion for reciprocating motion toward and away from said sensing face through said field when the same is present, the metal disk being disposed between said abutment means and said sensing face and the abutment means functioning to prevent the metal disk from sliding off of the post portion and the weight and cross-sectional area of said metal disk permitting the same to be moved on said post portion by the flow of air.

5. Air flow sensor means comprising:
   a proximity switch having a housing, one end of said housing being a sensing face and having means to develop an electrical field in a zone adjacent the sensing face;
   an end piece including a post portion, the end piece extending away from said sensing face outwardly through said field when the same is present;
   abutment means on said post portion; and
   disk means mounted on said post portion for reciprocating motion toward and away from said sensing face through said field when the same is present, the disk means being disposed between said abutment means and said sensing face and the abutment means functioning to prevent the disk means from sliding off of the post portion and the weight and cross-sectional area of the disk means permitting the same to be moved on said post portion by the flow of air.

6. The flow-sensor means according to claims 1, 2, 3, or 4 further including helical spring means made of non-magnetic material disposed between said abutment means and said metal disk which urges the metal disk toward said sensing face and which provides for the metal disk to move toward the abutment means under the influence of air flow.

7. Air flow sensor means comprising:
a proximity switch having a housing, one end of said housing being a sensing face and having means to develop an electrical field in a zone adjacent the sensing face;
disk means; and
means mounting said disk means adjacent said one end for reciprocating motion toward and away from said sensing face through said field when the same is present to respective positions inside and outside the effective zone of said field.

8. Equipment for use on the face of a person to provide a signal each time the person inhales or exhales, the equipment comprising:
a hollow, flexible mask to fit over the face of a person and form a chamber covering the nose and mouth of the person whereby air exhaled or inhaled will pass through the chamber;
check valve means on the mask which opens when the person exhales to provide for the flow of air from inside the mask to the outside of the mask and which closes when the person inhales;
an air intake tube formed on the mask;
an elongated tubular member having a top section and a bottom section, the top section extending into said air intake tube and secured thereto and being open to the interior of the mask to form a mask air inlet, the top section having a shoulder and a plurality of air inlet means formed intermediate the shoulder and the bottom section;
an air flow sensor including a proximity switch having a housing, one end of which is a sensing face disposed closely adjacent said shoulder, means to develop a magnetic field in a zone adjacent the sensing face, a metal disk mounted for reciprocating motion toward and away from said shoulder through said field when the same is present, and abutment means to limit movement in a direction away from said shoulder;
the housing being connected with the bottom section of said tubular member and extending through the tubular member and spaced from the inside thereof to form an air passageway between said air inlet means and said mask air inlet;
said air inlet means, said air passageway, and said mask air inlet providing for outside air to flow through the air inlet means, said air passageway and through said mask air inlet into the mask and the weight and cross-sectional area of the metal disk providing for the disk to function as follows:
  (a) when the patient inhales and air flows through the air inlet means, the air passageway, and the mask air inlet, the air flow lifts the metal disk away from said shoulder; and
  (b) when the patient stops inhaling and said flow ceases, the disc moves down on said shoulder and remains on said shoulder while the patient exhales.

9. Equipment for use on the face of a person to provide a signal each time the person inhales or exhales, the equipment comprising:
a hollow, flexible mask to fit over the face of a person and form a chamber covering the nose and mouth of the person whereby air exhaled or inhaled will pass through the chamber;
check valve means on the mask which opens when the person exhales to provide for the flow of air from inside the mask to the outside of the mask and which closes when the person inhales;
an air intake tube formed on the mask;
an elongated tubular member having a top section and a bottom section and a plurality of air inlet means formed intermediate the top and bottom sections, the top section extending into said air intake tube and secured thereto and being open to the interior of the mask to form a mask air inlet;
an air flow sensor including a proximity switch having a housing one end of which is a sensing face and having means to develop a magnetic field in a zone adjacent the sensing face, a metal disk mounted for reciprocating motion toward and away from said sensing face between a position adjacent the sensing face and a position away from the sensing face through said field when the same is present, and abutment means to limit said movement of the metal disk;
the housing being connected with the bottom section of said tubular member and extending through the tubular member and spaced from the inside thereof to form an air passageway between said air inlet means and said mask air inlet;
said air inlet means, said air passageway, and said mask air inlet providing for outside air to flow through the air inlet means, said air passageway and through said mask air inlet into the mask and the weight and cross-sectional area of the metal disk providing for the disk to function as follows:
  (a) when the patient inhales and air flows through the air inlet means, the air passageway, and the mask air inlet, the air flow lifts the metal disk to a position away from said sensing face; and
  (b) when the patient stops inhaling and said flow ceases, the disk moves down to a position adjacent said sensing face and remains in said last position while the patient exhales.

10. Equipment for use on the face of a person to provide a signal each time the person inhales or exhales, the equipment comprising:
a hollow, flexible mask to fit over the face of a person and form a chamber covering the nose and mouth of the person whereby air exhaled or inhaled will pass through the chamber;
check valve means on the mask which opens when the person exhales to provide for the flow of air from inside the mask to the outside of the mask and which closes when the person inhales;
an air intake tube formed on the mask;
an elongated tubular member having a top section and a bottom section and a plurality of air inlet means formed intermediate the top and bottom sections, the top section extending into said air intake tube and secured thereto and being open to the interior of the mask to form a mask air inlet;
an air flow sensor including a proximity switch having a housing, one end of said housing being a sensing face and having means to develop a magnetic field in a zone adjacent the exterior of the sensing face, disk means mounted for reciprocating motion toward and away from said sensing face between a position adjacent the sensing face and a position away from the sensing face through said field when the same is present, and abutment means to limit said movement of the disk means;

the housing being connected with the bottom section of said tubular member and extending through the tubular member and spaced from the inside thereof to form an air passageway between said air inlet means and said mask air inlet;

said air inlet means, said air passageway, and said mask air inlet providing for outside air to flow through the air inlet means, said air passageway and through said mask air inlet into the mask and the weight and cross-sectional area of the disk means providing for the disk means to function as follows:

(a) when the patient inhales and air flows through the air inlet means, the air passageway, and the mask air inlet, the air flow lifts the disk means to a position away from said sensing face; and (b) when the patient stops inhaling and said flow ceases, the disk means moves down to a position adjacent said sensing face and remains in said last position while the patient exhales.

11. In equipment to provide a signal each time a person inhales or exhales during breathing comprising:

a hollow flexible mask to fit over the face of a person and form a chamber covering the nose and mouth of the person whereby air exhaled or inhaled will pass through the chamber;

check valve means on the mask which opens when the person exhales to provide for the flow of air from inside the mask to the outside of the mask and closes when the person inhales;

an air intake tube formed on the mask the air intake tube having an axis;

support means connected to said air intake tube;

air flow sensor means connected to said support means to provide a signal each time a person inhales or exhales;

a pair of mercury switches mounted on said support means each including liquid mercury, contacts, and an elongated housing containing the mercury and the contacts the elongated housing having an axis;

the mercury switches being disposed opposite one another on opposite sides of the axis of said air intake tube and oriented so that the projection of the axis of each housing intersects first and second planes oriented at right angles to one another and intersecting each other along the axis of the tubular member;

said orientation of the mercury switches providing that:

(a) when the patient is upright the mercury in both switches closes the contacts;

(b) when the patient is lying horizontally face up, the mercury in both switches opens the contacts; and (c) when the patient is lying horizontally, face to the side, the mercury in the lowermost switch opens the contacts and the mercury in the other switch closes the contacts;

the mercury switch being for use in generating signals respectively that the patient has assumed the position of (a), (b), and (c).

* * * * *